US008552055B2

(12) United States Patent
De Saizieu et al.

(10) Patent No.: US 8,552,055 B2
(45) Date of Patent: *Oct. 8, 2013

(54) DIETARY AND PHARMACEUTICAL COMPOSITIONS CONTAINING TRICYCLIC DITERPENES AND THEIR DERIVATES AND THEIR USES

(75) Inventors: Antoine De Saizieu, Brunstatt (FR); Ann Fowler, Rheinfelden (CH); Regina Goralczyk, Grenzach-Wyhlen (DE); Claus Kilpert, Mannheim (DE); Goede Schueler, Eimeldingen (DE); Christof Wehrli, Witterswil (CH)

(73) Assignee: DSM IP Assets B.V., Te Heerlen (NL)

( * ) Notice: Subject to any disclaimer, the term of this patent is extended or adjusted under 35 U.S.C. 154(b) by 194 days.

This patent is subject to a terminal disclaimer.

(21) Appl. No.: 12/654,596

(22) Filed: Dec. 23, 2009

(65) Prior Publication Data
US 2010/0099753 A1    Apr. 22, 2010

Related U.S. Application Data

(62) Division of application No. 12/297,416, filed as application No. PCT/EP2007/010132 on Nov. 22, 2007, now abandoned.

(30) Foreign Application Priority Data

Nov. 24, 2006   (EP) .................................... 06024385

(51) Int. Cl.
| | | |
|---|---|---|
| A01N 43/02 | (2006.01) | |
| A01N 37/10 | (2006.01) | |
| A61K 31/235 | (2006.01) | |
| A61K 31/19 | (2006.01) | |

(52) U.S. Cl.
USPC ........... 514/449; 514/532; 514/557; 514/680; 514/729

(58) Field of Classification Search
USPC .................................. 514/449, 532, 557, 680
See application file for complete search history.

(56) References Cited

U.S. PATENT DOCUMENTS

| | | | | |
|---|---|---|---|---|
| 5,256,700 | A * | 10/1993 | Aeschbach et al. | ........... 514/732 |
| 6,579,543 | B1 | 6/2003 | McClung | |
| 6,638,523 | B1 | 10/2003 | Miyazaki et al. | |
| 2001/0056121 | A1 * | 12/2001 | Kosaka et al. | ................ 514/570 |

FOREIGN PATENT DOCUMENTS

| | | |
|---|---|---|
| CN | 1 145 790 | 3/1997 |
| CN | 1 478 506 | 3/2004 |
| CN | 1 682 930 | 10/2005 |
| CN | 1 723 997 | 1/2006 |
| KR | 2001 062 277 | 7/2001 |

OTHER PUBLICATIONS

Quigley (2002) Health behavior News Service.*
Mora et al. J. Ethanopharmacolgy 106 (2006) 76-81.*
Freedictionary .con (3pages) 2004.*
Herrera-Ruiz et al, "Antidepressant and anxiolytic effects of hydroalcoholic extract from *Salvia elegans*", Journal of Ethnopharmacology, vol. 107, 1, Aug. 11, 2006, pp. 53-58.
International Search Report for PCT/EP2007/010132, mailed Nov. 22, 2007.
Mora et al., "The hydroalcoholic extract of *Salvia elegans* induces anxiolytic- and antidepressant-like effects in rats", Journal of Ethnopharmacology, vol. 106, No. 1, pp. 76-81, (Jun. 15, 2006).
Frishman W. H. et al., "The use of herbs for treating cardiovascular disease", Seminars in Integrative Medicine, vol. 2, No. 1, pp. 23-35, (Mar. 2004).
English translation of Makino et al, "Aroma Components of Pineapple-Scented Sage (*Salvia Elegans* Vahl)", Foods Food Ingredients Journal (Japan) No. 169 (1996) 121-124.
Kennedy, D.O., et al; "Effects of Cholinesterase Inhibiting Sage (*Salvia officinals*) on Mood, Anxiety and Performance on a Psychological Stressor Battery"; *Neuropsychopharmacology*, vol. 31, pp. 845-852 (2006).
Kosaka, K., et al; "Carnosic Acid, a Component of Rosemary (*Rosmarinus officinals* L.), Promotes Synthesis of Nerve Growth Factor in T98G Human Glioblastoma Cells"; *Biol. Pharm. Bull.*, vol. 26, No. 11, pp. 1620-1622 (2003).

* cited by examiner

*Primary Examiner* — Shirley V Gembeh
(74) *Attorney, Agent, or Firm* — Nixon & Vanderhye P.C.

(57) ABSTRACT

The present invention refers to tricyclic diterpenes and their derivatives of the formulae (I) and (II), wherein $R^1$ is hydrogen or $C_{1-6}$-alkyl; $R^2$ is hydroxy, $C_{3-5}$-acyloxy, hydroxymethyl, 1,3-dihydroxypropyl or $C_{1-6}$-alkyl; $R^3$ and $R^4$ independently from each other are hydrogen, hydroxy, hydroxymethyl, $C_{1-5}$-acyloxy or $C_{1-6}$-alkoxy; $R^5$ is $C_{1-6}$-alkyl, hydroxymethyl carboxy or methoxycarbonyl; $R^9$ is hydrogen, hydroxymethyl, methoxy, oxo or $C_{1-5}$-acyloxy; $R^{10}$ is hydrogen, or $R^5$ and $R^9$ taken together are —$CH_2$—O— or —O—$CH_2$—; or $R^5$ and $R^{10}$ taken together are —CO—O—, —O—CO—, —$CH_2$—O— or —O—$CH_2$—; $R^6$ is hydrogen, or $R^5$ and $R^6$ together form a bond; $R^7$ and $R^8$ independently from each other are $C_{1-6}$-alkyl, carboxy, x-hydroxy-Cx-alkyl (with x being an integer from 1 to 6), or $C_{1-6}$-alkoxycarbonyl with the proviso that at least one of $R^7$ and $R^8$ is $C_{1-6}$-alkyl; $R^{11}$ and $R^{12}$ are both hydrogen or $R^{11}$ and $R^{12}$ together are oxo, with the further proviso for formula (I) that if $R^2$ is hydroxy $R^1$ is $C_{1-6}$-alkyl, for use as medicaments for the treatment of a disorder connected to impaired neurotransmission, as well as to dietary and pharmaceutical compositions and their uses.

12 Claims, 3 Drawing Sheets

DIETARY AND PHARMACEUTICAL COMPOSITIONS CONTAINING TRICYCLIC DITERPENES AND THEIR DERIVATES AND THEIR USES

This application is a divisional of application Ser. No. 12/297,416 filed Oct. 16, 2008 now abandoned which in turn is the U.S. national phase of International Application No. PCT/EP2007/010132, filed 22 Nov. 2007, which designated the U.S. and claims priority to Europe Application No. 06024385.4, filed 24 Nov. 2006, the entire contents of each of which are hereby incorporated by reference.

BRIEF DESCRIPTION OF THE INVENTION

The present invention refers to tricyclic diterpenes and their derivatives for use as medicaments, especially for the treatment of disorders connected to impaired or reduced neurotransmission, as well as to dietary and pharmaceutical compositions containing such tricyclic diterpenes and their derivatives and their uses.

BACKGROUND OF THE INVENTION

It is well known that impaired neurotransmission, e.g. low neurotransmitter levels, is connected to mental diseases such as depression and generalized anxiety disorders (GAD), and increased susceptibility to stress.

Compounds that increase neurotransmitter levels in the brain and thus enhance their transmission, can exhibit antidepressant properties as well as beneficial effects on a variety of other mental disorders (*Neurotransmitters, drugs and brain function*, R. A. Webster (ed), John Wiley & Sons, New York, 2001, p. 187-211, 289-452, 477-498). The main neurotransmitters are serotonin, dopamine, noradrenaline (=norepinephrine), acetylcholine, glutamate, gamma-aminobutyric acid, as well as neuropeptides. Those neurotransmitters of particular relevance to mood-related disorders include serotonin, noradrenaline and dopamine. Enhanced or prolonged neurotransmission is achieved by increasing the concentration of the neurotransmitter in the synaptic cleft, through inhibition of re-uptake into the pre-synaptic nerve ending, or by preventing neurotransmitter catabolism by inhibition of degrading enzymes such as monoamine oxidases (MAOs)-A and -B.

Antidepressants and Mood-Related Disorders

Tricyclic antidepressant compounds (TCAs), such as imipramine, amitriptyline and clomipramine, inhibit the re-uptake of serotonin and noradrenaline. They are widely regarded as among the most effective antidepressants available, but they have a number of disadvantages because they additionally interact with muscarinic acetylcholine-, histamine- and serotonin-receptors. Side effects resulting from such activities include dry mouth, blurred vision, constipation and urinary retention, in addition to postural hypotension. Most importantly, TCAs are not safe when taken in overdose, frequently showing acute cardiotoxicity.

Another class of antidepressant drugs are the so-called SSRIs (selective serotonin re-uptake inhibitors) including fluoxetine, paroxetine, sertraline, citalopram and fluvoxamine, that block the serotonin transporter (SERT), a high affinity sodium chloride-dependent neurotransmitter transporter that terminates serotonergic neurotransmission by re-uptake of serotonin. They have been proven as effective in the treatment of depression and anxiety as TCAs, but are usually better tolerated. These medications are typically started at low dosages and are increased until they reach a therapeutic level. A common side effect is nausea. Other possible side effects include decreased appetite, dry mouth, sweating, infection, constipation, tremor, yawning, sleepiness and sexual dysfunction.

In addition, compounds that prevent the catabolism of neurotransmitters more broadly by inhibiting MAOs-A and -B exhibit antidepressant effects. MAOs catalyse the oxidation of amine group-containing neurotransmitters, such as serotonin, noradrenaline and dopamine.

Furthermore, modulators of neurotransmission exert pleiotropic effects on mental and cognitive functions.

There is a need for compounds for the treatment or prevention of mental diseases and/or disorders which do not show the negative side effects of known antidepressants. Many patients are interested in alternative therapies which could minimize the side effects associated with high-dose of drugs and yield additive clinical benefits. Severe depression is a long lasting and recurring disease, which is usually poorly diagnosed. Furthermore many patients suffer from mild or middle severe depression. Thus, there is an increasing interest in the development of compounds as well as pharmaceutical and/or dietary compositions that may be used to treat mental diseases/disorders or to prevent the development of mental diseases/disorders such as depression and dysthymia in people at risk, to stabilize mood and achieve emotional balance.

In addition, patients often suffer either as a comorbidity to depression, or by itself from generalized anxiety syndrome (GAD). GAD is a highly prevalent anxiety condition and chronic illness in primary care (~10% of patients) (Wittchen, et al 2005 *Eur. Neuropsychopharm.* 15:357-376). Patients present themselves to their primary care physician with multiple physical symptoms. GAD is characterized by chronic tension, and anxious worrying and tension (>6 months), which are disabling and uncontrollable, and accompanied by a characteristic hypervigilance syndrome (including restlessness, muscle tension, and sleep problems). If untreated, GAD runs a chronic, fluctuating course and tends to get more severe with age. GAD patients suffer from subsyndromal depression and contribute to the highest overall direct and indirect health economic burden of all anxiety and depressive disorder. Despite high GAD incidence, few sufferers are diagnosed, prescribed medication, or receive psychiatric referral-simple diagnostic tools to aid patient recognition and monitoring are needed. Regardless of specific diagnosis, physicians require effective GAD-symptom treatments. SSRIs such as paroxetine are effective for GAD treatment [Stocchi et al. 2003, *J Clin Psych*, 63(3):250-258. Also, systematic reviews and placebo-controlled RCTs (Randomized Clinical Trials) indicate that some SSRIs (escitalopram, paroxetine and sertraline), the SNRI (Selective Norepinephrine Reuptake Inhibitors) venlafaxine, some benzodiazepines (alprazolam and diazepam), the tricyclic imipramine, and the 5-HT1A partial agonist buspirone are all efficacious in acute treatment. In general, the effect of treatment is often moderate and symptoms reappear when the treatment period is discontinued. Therefore, a continuous long-term treatment or prevention with compounds which have fewer side effects than SSRIs and can be taken over long time periods might be favourable over drug treatment.

Mood disorders and occupational stress also lead to consecutive sleep disorders, insomnia, low sleep quality, disturbances in circadian rhythms. These conditions are often chronic and can persist over long time. Also, deregulation of circadian rhythms induced by long-term flights (jet-lag) as well as by shift-working can cause similar symptoms and distress. Therefore, treatment with dietary supplementation to alleviate and prevent symptoms associated with the sleep disorders, such as impairment of cognitive function and memory, mental and physical fatigue, dreaminess, is warranted to improve the overall quality of life and benefiting vital energy of a person in need thereof.

DETAILED DESCRIPTION OF THE INVENTION

It has been found that tricyclic diterpenes and their derivatives of the formulae I and II, wherein $R^1$ is hydrogen or $C_{1-6}$-alkyl;
$R^2$ is hydroxy, $C_{3-5}$-acyloxy, hydroxymethyl, 1,3-dihydroxypropyl or $C_{1-6}$-alkyl;
$R^3$ and $R^4$ are independently from each other hydrogen, hydroxy, hydroxymethyl (—CH$_2$—OH), $C_{1-5}$-acyloxy or $C_{1-6}$-alkoxy;
$R^5$ is $C_{1-6}$-alkyl, hydroxymethyl, carboxy (CO$_2$H) or methoxycarbonyl (CO$_2$CH$_3$);
$R^9$ is hydrogen, hydroxymethyl, methoxy, oxo or $C_{1-5}$-acyloxy;
$R^{10}$ is hydrogen; or
$R^5$ and $R^9$ taken together are —CH$_2$—O— or —O—CH$_2$—;
or $R^5$ and $R^{10}$ taken together are —CO—O—, —O—CO—, —CH$_2$—O— or —O—CH$_2$—;
$R^6$ is hydrogen, or $R^5$ and $R^6$ together form a bond;
$R^7$ and $R^8$ are independently from each other $C_{1-6}$-alkyl, carboxy, x-hydroxy-$C_x$-alkyl (with x being an integer from 1 to 6), or $C_{1-6}$-alkoxycarbonyl (—CO$_2$(C$_{1-6}$-alkyl)) with the proviso that at least one of $R^7$ and $R^8$ is $C_{1-6}$-alkyl;
$R^{11}$ and $R^{12}$ are both hydrogen or $R^{11}$ and $R^{12}$ together are oxo;
with the further proviso for formula I that if $R^2$ is hydroxy $R^1$ is $C_{1-6}$-alkyl can be used in medicaments for the treatment of impaired or reduced neurotransmission.

Preferred are tricyclic diterpenes and their derivatives that give positive results for inhibition of hSERT dependent uptake of tritiated serotonin into transfected cells, transfected with the human serotonin transporter.

Especially preferred are tricyclic diterpenes and their derivatives of formulae I and II,
wherein $R^1$ is hydrogen or iso-propyl;
$R^2$ is hydroxy or iso-propyl;
$R^3$ and $R^4$ are independently from each other hydrogen, hydroxy or methoxy;
$R^5$ is methyl or carboxy; $R^9$ is hydrogen, oxo or methoxy; $R^{10}$ is hydrogen; or
$R^5$ and $R^9$ taken together are —CH$_2$—O— or —O—CH$_2$—;
or $R^5$ and $R^{10}$ taken together are —CO—O—, —O—CO—, —CH$_2$—O— or —O—CH$_2$—;
$R^6$ is hydrogen, or $R^5$ and $R^6$ together form a bond;
$R^7$ and $R^8$ are independently from each other methyl, carboxy, hydroxymethyl or methoxycarbonyl with the proviso that at least one of $R^7$ and $R^8$ is methyl; with the further proviso for formula I that if $R^2$ is hydroxy $R^1$ is iso-propyl.

Figure 2:
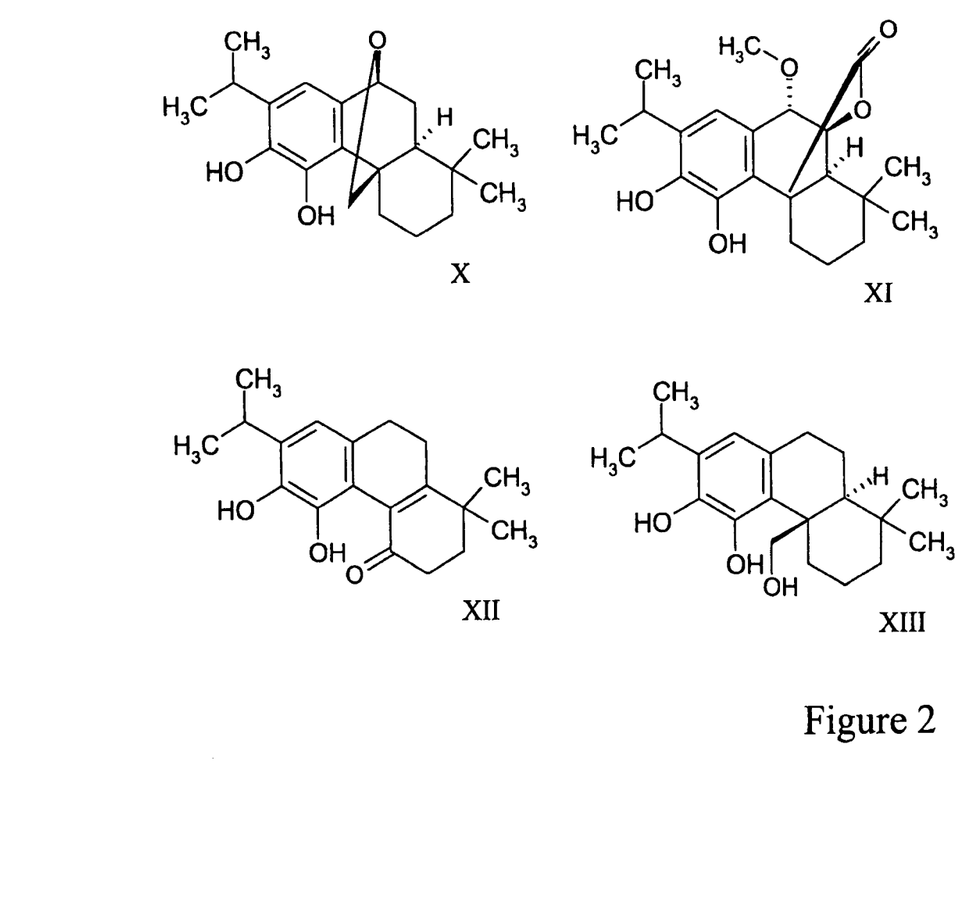
FIG. 2 shows compounds of the formulae X to XIII.
Figure 3:
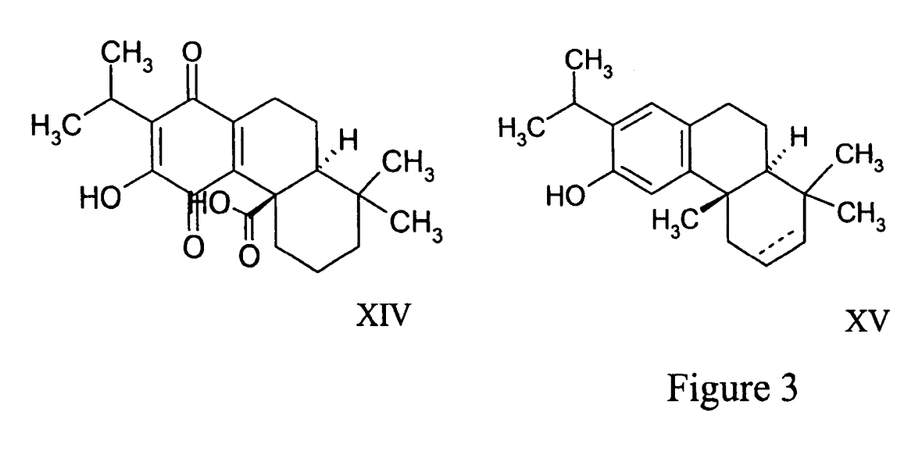

Thus, in one aspect the invention relates to tricyclic diterpenes and their derivatives of the formulae I and II, wherein $R^1$ is hydrogen or $C_{1-6}$-alkyl;
$R^2$ is hydroxy, $C_{1-5}$-acyloxy, hydroxymethyl, 1,3-dihydroxypropyl or $C_{1-6}$-alkyl;
$R^3$ and $R^4$ are independently from each other hydrogen, hydroxy, hydroxymethyl, $C_{1-5}$-acyloxy or $C_{1-6}$-alkyloxy;
$R^5$ is $C_{1-6}$-alkyl, hydroxymethyl or carboxy;
$R^9$ is hydrogen, hydroxymethyl, methoxy, oxo or $C_{1-5}$-acyloxy;
$R^{10}$ is hydrogen; or
$R^5$ and $R^9$ taken together are —CH$_2$—O— or —O—CH$_2$—;
or $R^5$ and $R^{10}$ taken together are —CO—O—, —O—CO—, —CH$_2$—O— or —O—CH$_2$—;
$R^6$ is hydrogen, or $R^5$ and $R^6$ together form a bond;
$R^7$ and $R^8$ are independently from each other $C_{1-6}$-alkyl, carboxy, x-hydroxy-$C_x$allyl (with x being an integer from 1 to 6), or $C_{1-6}$-alkoxycarbonyl with the proviso that at least one of $R^7$ and $R^8$ is $C_{1-6}$-alkyl;
$R^{11}$ and $R^{12}$ are both hydrogen or $R^{11}$ and $R^{12}$ together are oxo;
with the further proviso for formula I that if $R^2$ is hydroxy $R^1$ is $C_{1-6}$-alkyl;
preferably to tricyclic diterpenes and their derivatives of the formulae I and II, wherein
$R^1$ is hydrogen or iso-propyl;
$R^2$ is hydroxy or iso-propyl;
$R^3$ and $R^4$ are independently from each other hydrogen, hydroxy or methoxy;
$R^5$ is methyl or carboxy;
$R^9$ is hydrogen, oxo or methoxy;
$R^{10}$ is hydrogen or
$R^5$ and $R^9$ taken together are —CH$_2$—O— or —O—CH$_2$—;
or $R^5$ and $R^{10}$ taken together are —CO—O—, —O—CO—, —CH$_2$—O— or —O—CH$_2$—;

R⁶ is hydrogen, or R⁵ and R⁶ together form a bond;
R⁷ and R⁸ independently from each other are methyl, carboxy, hydroxymethyl or methoxycarbonyl, with the proviso that at least one of R⁷ and R⁸ is methyl; and with the further proviso for formula I that if R² is hydroxy, R¹ is iso-propyl;
more preferably to compounds of formulae III to VII and X to XV (see FIGS. 1, 2 and 3 below),
most preferably to carnosic acid (compound of formula III) and 7-oxocallitrisic acid (compound of formula IV), for use as medicament for the treatment of a disorder connected to impaired or reduced neurotransmission.

BRIEF DESCRIPTION OF THE FIGURES

FIG. 3 shows compounds of the formulae XIV and XV In another aspect, the invention relates to the use of a tricyclic diterpene and its derivative of the formulae I and II as defined above for the manufacture of a composition for the treatment of a disorder connected to impaired or reduced neurotransmission, particularly for the manufacture of an antidepressant, a mood/vitality improver, a stress reliever, a condition improver, a reducer of anxiety, a reducer of obsessive-compulsive behaviour, a relaxant, a sleep improver and/or a insomnia alleviator.

In still another aspect, the invention relates to a dietary composition containing at least one tricyclic diterpene or its derivative of the formulae I and II as defined above as well as to a pharmaceutical composition containing at least one tricyclic diterpene or its derivative of the formulae I and II as defined above and a conventional pharmaceutical carrier.

Further, the invention relates to a method for the treatment of a disorder connected to impaired or reduced neurotransmission in animals including humans, said method comprising administering an effective dose of a tricyclic diterpene and/or a derivative thereof according to formulae I and II as defined above to animals including humans which are in need thereof.

Animals in the context of the present invention include humans and encompass mammals, fish and birds. Preferred "animals" are humans, pet and companion animals and farm animals. Examples of pet and companion animals are dogs, cats, birds, aquarium fish, guinea pigs, (jack) rabbits, hares and ferrets. Examples of farm animals are aquaculture fish, pigs, horses, ruminants (cattle, sheep and goats) and poultry.

Figure 1:
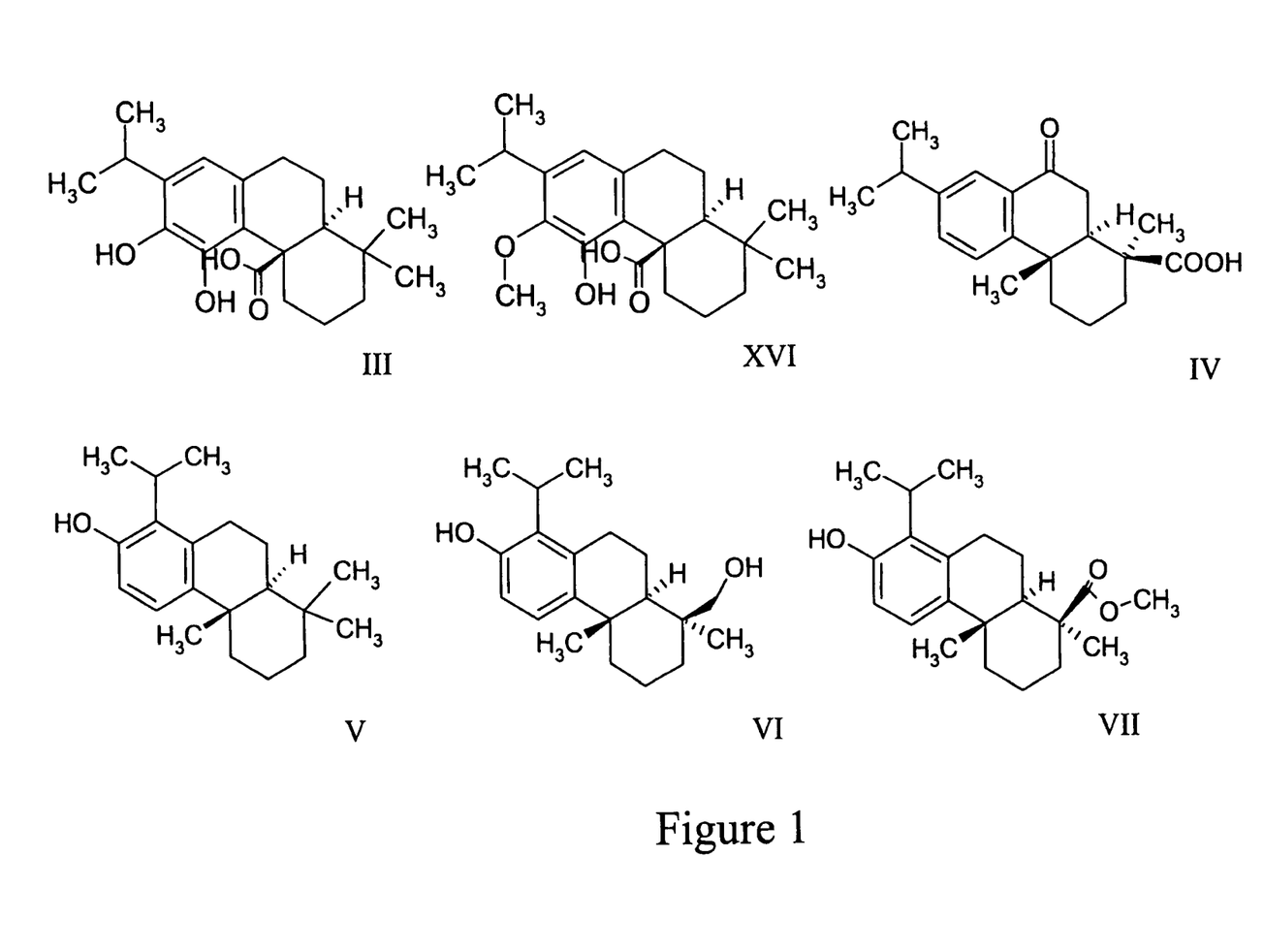
FIG. 1 shows compounds of the formulae III to VII and XVI.

In a preferred aspect of the present invention the tricyclic diterpene and its derivative of the formulae I is selected from the group consisting of:
carnosic acid (compound of the formula III; see FIG. 1),
7-oxocallitrisic acid (compound of the formula IV; see FIG. 1),
totarol (compound of the formula V; see FIG. 1),
16-hydroxytotarol (compound of the formula VI; see FIG. 1),
totarol-19-carboxylic acid methyl ester (compound of the formula VII; see FIG. 1),
20-deoxo-carnosol (compound of the formula X; see FIG. 2),
7-methylrosmanol (compound of the formula XI; see FIG. 2),
sageone (compound of the formula XII; see FIG. 2),
8,11,13-abietatriene-11,12,20-triol (compound of the formula XIII; see FIG. 2),
royleanonic acid (compound of the formula XIV; see FIG. 3),
ferruginol (compound of the formula XV; see FIG. 3) and
carnosic acid 12-methyl ether (compound of the formula XVI; see FIG. 1).

More preferred tricyclic diterpenes of the formula I are: carnosic acid, 7-oxocallitrisic acid and 20-deoxo-carnosol. Even more preferred are carnosic acid, and 7-oxocallitrisic acid, and most preferred is (4aR,10aS)-carnosic acid.

The term "tricyclic diterpene and its derivative of the formulae I and II" also encompasses any material or extract of a plant containing such a tricyclic diterpene and a derivative thereof according to formulae I and II in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract. The terms "material of a plant" and "plant material" used in the context of the present invention mean any part of a plant.

"Carnosic acid" means the racemic mixture as well as pure (4aR,10aS)-carnosic acid or pure (4aS,10aR)-carnosic acid or any mixture or diastereoisomer of them. Carnosic acid can be isolated from plants like rosemary and sage, but not limited to these. "Carnosic acid" means both "natural" (isolated) and "synthetic" (manufactured) carnosic acid. Carnosic acid synthesis is described in *Chin Chem Lett* 2001, 12(3), 203-204 (ISSN: 1001-8417).

Therefore, any material or extract of rosemary or sage, or any other plant material or extract containing carnosic acid in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression.

"Carnosic acid 12-methyl ether" means the racemic mixture as well as pure (4aR,10aS)-carnosic acid 12-methyl ether or pure (4aS,10aR)-carnosic acid 12-methyl ether or any mixture or diastereoisomer of them. Carnosic acid 12-methyl ether can be isolated from plants like sage, rosemary, *Hyptis martiusii*, but is not limited to these. "Carnosic acid 12-methyl ether" means both "natural" (isolated) and "synthetic" (manufactured) carnosic acid 12-methyl ether.

Therefore, any material or extract of these plants or any other plant material or extract containing carnosic acid 12-methyl ether in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression.

"7-Oxocallitrisic acid" means the racemic mixture as well as pure (1S,4aS,10aR)-7-oxo-callitrisic acid or pure (1R,4aR,10aS)-7-oxocallitrisic acid or any mixture or diastereoisomer of them. 7-Oxocallitrisic acid can be isolated from plants such as, but not limited to: *Cynara cardunculus* ssp. *Cardunculus* and *Juniperus chinensis*. Therefore, any material or extract of these plants or any other plant material or extract containing 7-oxocallitrisic acid in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "7-Oxocallitrisic acid" means both "natural" (isolated) and "synthetic" (manufactured) 7-oxocallitrisic acid.

"Totarol" means the racemic mixture as well as pure (4bS, 8aS)-totarol ((+)-totarol, trans-totarol) or pure (4bR,8aR)-totarol or any mixture or diastereoisomer of them. Totarol can be isolated from plants such as, but not limited to sage, juniper and *Podocarpus* sp. Therefore, any material or extract of these plants or any other plant material or extract containing totarol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression.

"Totarol" means both "natural" (isolated) and "synthetic" (manufactured) totarol. Totarol synthesis is described in several articles, i.e. in *Tetrah. Lett.* 2003, 44(49):8831-8835.

"16-Hydroxytotarol" means the racemic mixture as well as pure (1S,4aS,10aR)-16-hydroxytotarol or pure (1R,4aR, 10aS)-16-hydroxytotarol or any mixture or diastereoisomer of them. 16-Hydroxytotarol can be isolated from the wood of *Podocarpus* species and other plants. Therefore, any material or extract of these plants or any other plant material or extract containing 16-hydroxytotarol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "16-Hydroxytotarol" means both "natural" (isolated) and "synthetic" (manufactured) 16-hydroxytotarol. 16-hydroxytotarol synthesis is described in several articles, i.e. in *J. Chem Soc,* 1963 (Abstracts), 1553-1560 and in *Chem & Ind* 1963 44: 1760-1761.

"Totarol-19-carboxylic acid methyl ester" means the racemic mixture as well as pure (4aR,10aS)-totarol-19-carboxylic acid methyl ester or pure (4aR,10aS)-totarol-19-carboxylic acid methyl ester or any mixture or diastereoisomer of them. Totarol-19-carboxylic acid methyl ester can be isolated from the wood of *Podocarpus* species and other plants. Therefore, any material or extract of these plants or any other plant material or extract containing totarol-19-carboxylic acid methyl ester in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "Totarol-19-carboxylic acid methyl ester" means both "natural" (isolated) and "synthetic" (manufactured) totarol-19-carboxylic acid methyl ester. Totarol-19-carboxylic acid methyl ester can be prepared according to the process described in *Chem & Ind* 1963, 44: 1760-1761.

"20-Deoxo-carnosol" means the racemic mixture as well as pure (4aR,9S,10aS)-20-deoxo-carnosol or pure (4aS,9R, 10aR)-20-deoxo-carnosol or any mixture or diastereoisomer of them. 20-Deoxo-carnosol can be isolated from plants such as, but not limited to *Lepechinia urbaniana* and wild sage. Therefore, any material or extract of these plants or any other plant material or extract containing 20-deoxo-carnosol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "20-Deoxo-carnosol" means both "natural" (isolated) and "synthetic" (manufactured) 20-deoxo-carnosol.

"7-Methylrosmanol" means the racemic mixture as well as pure (4aR,9S,10S,10aS)-7-methylrosmanol or pure (4aS,9R, 10R,10aR)-7-methylrosmanol or any mixture or diastereoisomer of them. 7-Methylrosmanol can be isolated from plants such as, but not limited to rosemary, *Hyptis dilatata, Salivia* sp. and *Lepechinia* sp. Therefore, any material or extract of these plants or any other plant material or extract containing 7-methylrosmanol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "7-Methylrosmanol" means both "natural" (isolated) and "synthetic" (manufactured) 7-methylrosmanol. 7-Methylrosmanol's synthesis is described e.g. in *J. Nat. Prod.* 2002, 65(7):986-989.

Sageone can be isolated from plants such as sage, and other *Salvia* sp. Therefore, any material or extract of these plants or any other plant material or extract containing sageone in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "Sageone" means both "natural" (isolated) and "synthetic" (manufactured) sageone. Sageone synthesis is described e.g. in *J Org Chem* 1997 62(20):6928-6951.

"8,11,13-Abietatriene-11,12,20-triol" means the racemic mixture as well as pure (4bR,8aS)-8,11,13-abietatriene-11, 12,20-triol or pure (4bS,8aR)-8,11,13-abietatriene-11,12,20-triol or any diastereoisomer or mixture of them. 8,11,13-Abietatriene-11,12,20-triol can be isolated from plants including Salivia sp. Therefore, any material or extract of these plants or any other plant material or extract containing 8,11,13-abietatriene-11,12,20-triol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "8,11,13-Abietatriene-11,12,20-triol" means both "natural" (isolated) and "synthetic" (manufactured) 8,11,13-abietatriene-11,12,20-triol.

"Royleanonic acid" means the racemic mixture as well as pure (4aR,10aS)-royleanonic acid or pure (4aS,10aR)-royleanonic acid or any diastereoisomer or mixture of them. Royleanonic acid can be isolated from plants such as sage (*Salvia* sp.), but is not limited to it.

Therefore, any material or extract of these plants or any other plant material or extract containing royleanonic acid in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression.

"Royleanonic acid" means both "natural" (isolated) and "synthetic" (manufactured) royleanonic acid.

"Ferruginol" means pure (4bS,8aS)-ferruginol or pure (4bR,8aR)-ferruginol or any stereoisomer or mixture of them. Ferruginol can be isolated from plants like *Cryptomeria* sp., *Juniperus* sp. and *Salvia* sp., but is not limited to these.

Therefore, any material or extract of these plants or any other plant material or extract containing ferruginol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "Ferruginol" means both "natural" (isolated) and "synthetic" (manufactured) ferruginol. Ferruginol synthesis is described in *Org. Let.* 2001, 3(11): 1737-1740.

Beside the (pure) compounds carnosic acid, carnosic acid 12-methyl ether, 7-oxocallitrisic acid, totarol, 16-hydroxytotarol, totarol-19-carboxylic acid methyl ester, 20-deoxo-carnosol, 7-methylrosmanol, sageone, 8,11,13-abietatriene-11, 12,20-triol, royleanonic acid and ferruginol, especially preferred are plant materials and plant extracts containing at least 30 weight-% (i.e. from 30 to 100 weight-%), preferably at least 50 weight-% (i.e. from 50 to 100 weight-%), more preferably at least 70 weight-% (i.e. from 70 to 100 weight-%), most preferably at least 90 weight-% (i.e. from 90 to 100 weight-%), of these compounds, based on the total weight of the plant material/extract.

According to the present invention not only the tricyclic diterpenes and their derivatives of the formulae I and II themselves, with the definitions of $R^1$ to $R^{12}$ and the preferences as given above, but also plant materials and extracts containing them in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, as well as dietary and pharmaceutical compositions containing them can be used as medicament, especially for the treatment of a disorder connected to impaired or reduced neurotransmission.

In the context of this invention "treatment" also encompasses co-treatment as well as prevention. "Prevention" can be the prevention of the first occurrence (primary prevention) or the prevention of a reoccurence (secondary prevention).

Thus, the present invention is also directed to a method for the prevention of a disorder connected to impaired neurotransmission in animals including humans, said method comprising administering an effective dose of a tricyclic diterpene or its derivative of the formulae I and II, to animals including humans which are in need thereof. In this regard an effective may especially be used for maintaining the mental well-being, for maintaining a balanced cognitive function, for helping to reduce the risk of mood swings, for helping to retain a positive mood and for supporting cognitive wellness, and for helping to maintain a good sleep quality.

In the context of this invention the term "disorder" also encompasses diseases.

Medicaments/compositions for the treatment of disorders connected to impaired neurotransmission encompass antidepressants, mood/vitality improvers, stress relievers, condition improvers, anxiety reducers and obsessive-compulsive behaviour reducers, relaxants, sleep improvers and/or insomnia alleviators. They all improve, enhance and support the physiological neurotransmission, especially in the central nervous system, and therefore alleviate mental malfunction.

Antidepressants are medicaments/compositions for treating mental, behavioural and emotional/affective, neurotic, neurodegenerative, eating and stress related disorders such as e.g. unipolar depression, bipolar depression, acute depression, chronic depression, subchronic depression, dysthymia, postpartum depression, premenstrual dysphoria/syndrome (PMS), climacteric depressive symptoms, aggression, attention deficit disorders (ADS), social anxiety disorders, seasonal affective disorders, anxiety (disorders) such as generalized anxiety disorder (GAD), fibromyalgia syndrome, post-traumatic stress disorders, panic disorders, obsessive compulsive disorders, restless leg syndrome, nervousness, migraine/primary headaches and pain in general, emesis, bulimia, anorexia nervosa, binge eating disorder, gastrointestinal disorders, burn out syndrome, and irritability.

Antidepressants can also be used for (the manufacture of compositions for) primary and secondary prevention and/or the treatment of neurocognitive impairment. Furthermore they are also effective in the treatment of depressive symptoms or other symptoms related to disturbed neurotransmission occurring as comorbidity in chronic diseases such as cardiovascular diseases, strokes, cancer, Alzheimer disease, Parkinson disease, and others.

Thus, the tricyclic diterpenes or their derivatives of the formulae I and II with the definitions of $R^1$ to $R^{12}$ and the preferences as given above can be used in general as antidepressants for animals including humans, preferably for humans, pet animals and farm animals.

In a further embodiment of the present invention the tricyclic diterpenes or their derivatives find use as mood improver in general as well as for the manufacture of compositions for such use. "Mood improver" or "emotional wellness booster" or "vitality improver" means that the mood of a person treated with it is enhanced, that the self esteem is increased and/or that negative thoughts and/or negative tension are/is reduced. It also means the emotions are balanced and/or that the general, especially the mental, well being and vitality is improved or maintained, as well as that the risk of mood swings is (helped to be) reduced and that the positive mood is (helped to be) retained.

The tricyclic diterpenes or their derivatives of the formulae I and II with the definitions of $R^1$ to $R^{12}$ and the preferences as given above can also be used in general as "anxiety reducer" and/or "obsessive-compulsive behaviour reducer" for animals including humans, preferably for humans, pet animals and farm animals.

"Anxiety reducer" means that chronic tension and anxious worrying and tension are alleviated or relieved. Hypervigilance syndrome, including restlessness, muscle tension, and sleep problems are reduced or relieved. Social and other phobias are reduced or resolved. In general, the social environment is experienced less threatening. The person is emotionally relaxed, experiences comfort and enjoys company and contact to other people.

"Relaxant", "sleep improver" or "insomnia alleviator" means improving sleep onset and helping a person to easily enter sleep, to maintain undisrupted sleep throughout the night. It also means that circadian rhythm-associated sleep disturbances, due to jet-lag or shift work, are corrected and symptoms associated with sleeplessness, i.e. impairment of cognitive function and memory, mental and physical fatigue, dreaminess, are abolished or relieved and the overall quality of life and vital energy are improved.

Moreover, tricyclic diterpenes or their derivatives of the formulae I and II are useful for the treatment, prevention and the alleviation of stress related symptoms, for the treatment, prevention and alleviation of symptoms related to working overload, exhaustion and/or burn out, for the increase of the resistance or tolerance to stress and/or to favour and facilitate the relaxation in normal healthy individuals i.e. such compositions have an effect as "stress reliever".

A further embodiment of the present invention relates to the use of tricyclic diterpenes or their derivatives of the formulae I and II as "condition improvers", i.e. as means to reduce irritability and tiredness, to reduce or prevent or alleviate physical and mental fatigue, and to increase energy in more general terms, especially to increase the brain energy production, in diseased or normal healthy individuals. Moreover for cognition improvement in general, and especially for maintenance or improvement of attention and concentration, of the memory and of the capacity for remembering, of the learning ability, of the language processing, of problem solving and of intellectual functioning; for improvement of the short-term memory; for increasing the mental alertness; for enhancing the mental vigilance; for reducing the mental fatigue; for supporting cognitive wellness, for maintaining balanced cognitive function, for the regulation of hunger and satiety as well as for the regulation of motor activity.

Veterinary Uses

Pets and farm animals can be in conditions in need of enhanced or improved neurotransmission, which can be provided by the present invention. Animals may exhibit adverse behavioural and/or physiological reactions to stressful situations; animals raised in mass production environments, or being transported under unfavourable conditions, can display a decline in meat or milk quantity or quality; stressed poultry can resort to feather-picking, reduced egg laying and cannibalism. Many animals can become aggressive or display stereotypic-, anxiety- and obsessive-compulsive-behaviours under adverse housing or transport conditions.

Thus, another aspect of this invention is veterinary uses of tricyclic diterpenes or their derivatives of the formulae I and II as dietary/pharmaceutical compositions.

In a preferred embodiment of the present invention, tricyclic diterpenes or their derivatives of the formulae I and II, are administered for preventing stress in farm animals and mass production livestock husbandry, during transport to slaughter and/or for preventing loss of quality of meat of said farm animals under such circumstances. The farm animals are preferably poultry, cattle, sheep, goats and swine.

In another preferred embodiment of the present invention, tricyclic diterpenes or their derivatives of the formulae I and II are administered to poultry for preventing feather-picking and cannibalism resulting in, for example, loss of meat quality and egg production.

Another aspect of this invention is a method for preventing and/or alleviating stress in aquaculture, comprising administering tricyclic diterpenes or their derivatives of the formulae I and II, to animals which are in need thereof, wherein the animals are fish or shrimps.

In another preferred embodiment of the present invention, tricyclic diterpenes or their derivatives of the formulae I and II are administered to pets or companion animals for reduction of stress, tension and aggressiveness and compulsive behaviour exhibited under stressful conditions, such as separation, change or loss of owner, during holiday separation and husbandry in so-called "animal hotels" and husbandry in animal shelters or refuges.

Still another aspect of this invention is a method for preventing/reducing symptoms associated with stressful conditions in animals used in the fur industry, preferably minks, foxes and hares.

The term "dietary compositions" comprises any type of (fortified) food/feed and beverages including also clinical nutrition, and also dietary supplements. The dietary compositions according to the present invention may further contain protective hydrocolloids, binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellyfying agents, gel forming agents, antioxidants and antimicrobials.

Beside a pharmaceutically acceptable carrier and at least one tricyclic diterpene or a derivative thereof according to formulae I and II, the pharmaceutical compositions according to the present invention may further contain conventional pharmaceutical additives and adjuvants, excipients or diluents, flavouring agents, preservatives, stabilizers, emulsifying agents, buffers, lubricants, colorants, wetting agents, fillers, and the like. The carrier material can be organic or inorganic inert carrier material suitable for oral/parenteral/injectable administration.

The dietary and pharmaceutical compositions according to the present invention may be in any galenic form that is suitable for administrating to the animal body including the human body, especially in any form that is conventional for oral administration, e.g. in solid form such as (additives/supplements for) food or feed, food or feed premix, fortified food or feed, tablets, pills, granules, dragees, capsules, and effervescent formulations such as powders and tablets, or in liquid form such as solutions, emulsions or suspensions as e.g. beverages, pastes and oily suspensions. The pastes may be filled into hard or soft shell capsules. Examples for other application forms are forms for transdermal, parenteral or injectable administration. The dietary and pharmaceutical compositions may be in the form of controlled (delayed) release formulations.

Examples for fortified food are cereal bars, bakery items such as cakes and cookies.

Beverages encompass non-alcoholic and alcoholic drinks as well as liquid preparations to be added to drinking water and liquid food. Non-alcoholic drinks are e.g. soft drinks, sport drinks, fruit juices, lemonades, near-water drinks (i.e. water based drinks with a low calorie content), teas and milk based drinks. Liquid food are e.g. soups and dairy products (e.g. muesli drinks).

For humans a suitable daily dosage may be within the range of from 0.001 mg per kg body weight to about 20 mg per kg body weight per day. More preferred is a daily dosage of from about 0.01 to about 10 mg per kg body weight, and especially preferred is a daily dosage of from about 0.05 to 5.0 mg per kg body weight. The amount of a plant material or plant extract containing such tricyclic diterpene or a derivative thereof according to formulae I and II can be calculated accordingly.

In solid dosage unit preparations for humans, the tricyclic diterpene or the derivative thereof according to formulae I and II is suitably present in an amount in the range of from about 0.1 mg to about 1000 mg, preferably in the range of from about 1 mg to about 500 mg per dosage unit.

In dietary compositions, especially in food and beverages for humans, the tricyclic diterpene or the derivative thereof according to formulae I and II is suitably present in an amount in the range of from about 0.0001 (1 mg/kg) to about 5 weight-% (50 g/kg), preferably from about 0.001% (10 mg/kg) to about 1 weight-%, (10 g/kg) more preferably from about 0.01 (100 mg/kg) to about 0.5 weight-% (5 g/kg), based upon the total weight of the food or beverage.

In food and drinks in a preferred embodiment of the invention the amount of the tricyclic diterpene or the derivative thereof according to formulae I and II, is in the range of from 10 to 30 mg per serving, i.e. 120 mg per kg food or drink.

For animals excluding humans a suitable daily dosage of a tricyclic diterpene or a derivative thereof according to formulae I and II may be within the range of from 0.001 mg per kg body weight to about 1000 mg per kg body weight per day. More preferred is a daily dosage in the range of from about 0.1 mg to about 500 mg per kg body weight, and especially preferred is a daily dosage in the range of from about 1 mg to 100 mg per kg body weight.

The invention is illustrated further by the following examples.

EXAMPLES

The carnosic acid used in the experiments described below was obtained from Fluorochem, Wesley Street, Old Glossop, Derbyshire SK13 7RY, UK. The 7-oxocallitrisic acid was obtained from AnalytiCon Discovery GmbH, Hermannswerder Haus 17, 14473 Potsdam, Germany, and the totarol from Aldrich Chemical Company, Inc., 1001 West Saint Paul Avenue, Milwaukee, Wis. 53233, USA. The 16-hydroxytotarol and the Totarol-19-carboxylic acid methyl ester were obtained from MicroSource Discovery Systems Inc, 21 George Washington Plaza, Gaylordsville, Conn. 06755 USA.

The actions of the monoamine neurotransmitters, serotonin and dopamine, are regulated through their rapid uptake and clearance from synaptic junctions by plasma membrane transport proteins. The monoamine transporters in central monoaminergic neurones are responsible for the recovery of up to 90% of released neurotransmitter and are high affinity targets for a number of psychoactive agents such as cocaine, amphetamine and antidepressants. These agents, by blocking transporters and consequently preventing neuronal uptake, elevate levels of extracellular neurotransmitter concentrations in both the central and peripheral nervous systems, contributing to their behavioural and autonomic effects. Thus, inhibition of uptake of serotonin and dopamine by one or more of the compounds of interest is illustrated by the following two examples.

Example 1

Serotonin Uptake Inhibition by Tricyclic Diterpenes and their Derivatives of the Formula I HEK-293 cells stably expressing the human serotonin re-uptake transporter (hSERT) were obtained from R. Blakely, Vanderbilt University, USA. The cells were routinely grown in Dulbecco's Modified Eagle's Medium (Bioconcept) containing 10% fetal calf serum, penicillin, streptomycin, L-glutamine and the antibiotic G418 and passaged by trypsinisation. On the day of assay, cells from 80% confluent flasks were harvested by gentle washing with warm phosphate buffered saline (PBS). Cells were then washed once by centrifugation and re-suspended in Krebs Ringer bicarbonate buffer (Sigma) supplemented with 35 µM pargyline, 2.2 mM $CaCl_2$, 1 mM ascorbic acid and 5 mM N-2-hydroxyethylpiperazine-N'-2-ethanesulfonic acid (buffer called "Hepes") at a concentration of 10,000 cells in 160 µl of buffer, and aliquoted into round bottomed polypropylene 96 well microtitre plates (Corning) at 10,000 cells per well. Serotonin uptake into the cells was determined by addition of radio-labelled [$^3$H] serotonin (GE Healthcare) at a concentration of 20 nM, and incubation for 40 minutes at 37° C. with gentle shaking. At the end of this time unincorporated label was removed by filtration though Unifilter 96 GF/B plates (Perkin Elmer) using a Tomtec Mach III M cell harvester. The incorporated serotonin retained on the plates was quantified by liquid scintillation counting using Microscint-40/Topcount (Perkin Elmer).

The effect of the tricyclic diterpenes and their derivatives of the formula I, and of the reference compound, fluoxetine, on the serotonin uptake was determined by their inclusion in the assay at a range of concentrations (tricyclic diterpenes: 0.003-100 µM; fluoxetine: 0.03 nM-1 µM) for 10 minutes prior to and during the addition of [$^3$H] serotonin. Serotonin uptake via the transporter was inhibited by the tricyclic diterpenes and their derivatives of the formula I in a dose-dependent manner. The calculated $IC_{50}$ values for inhibition of serotonin uptake by tricyclic diterpenes and their derivatives of the formula I, and of fluoxetine, are shown in Table 1.

TABLE 1

Inhibition of serotonin uptake into transfected HEK-293 cells by tricyclic diterpenes and their derivatives of the formula I, and of the reference compound, fluoxetine.

| Substance | $IC_{50}$ [µM] for Tritiated Serotonin Uptake |
|---|---|
| Carnosic Acid | 36.4 ± 6.8 (n = 5) |
| 7-Oxocallitrisic Acid | 32.9 ± 8.6 (n = 3) |
| 16-Hydroxytotarol | 7.4 |
| Totarol-19-carboxylic acid methyl ester | 7.2 |
| Totarol | 7.5 ± 2.6 (n = 2) |
| 20-Deoxo-carnosol | 4.2 ± 0.2 (n = 2) |
| Carnosic acid-12-methylether | 22.0 ± 4.9 (n = 2) |
| Fluoxetine | 5 nM |

Results are shown as mean ± s.e.m., where measurements were repeated.

Example 2

Dopamine Uptake Inhibition by Carnosic Acid

CHO-Ki/hDAT cells expressing the human dopamine transporter (hDAT) were plated before the assay. Cells ($2 \times 10^5$/ml) were incubated with carnosic acid and/or vehicle in modified Tris-HEPES buffer, pH 7.1, at 25° C. for 20 minutes before addition of 50 nM [$^3$H]Dopamine for 10 minutes. Specific signal was determined in the presence of 10 µM nomifensine (dopamine reuptake inhibitor). Cells were then solubilised with 1% SDS lysis buffer. Reduction of [$^3$H] Dopamine uptake by 50 percent or more (≥50%) relative to vehicle controls indicated significant inhibitory activity. The compounds (nomifensine and carnosic acid) were screened at 10 concentrations up to 100 µM: 0.00316, 0.01, 0.0316, 0.1, 0.316, 1, 3.16, 10, 31.6 and 100 µM. These same concentrations were concurrently applied to a separate group of cells and evaluated for possible compound-induced cytotoxicity only if significant inhibition of uptake was observed.

TABLE 2

Measured $IC_{50}$ values for inhibition of dopamine reuptake into transfected CHO-Ki cells by carnosic acid and the reference compound, nomifensine.

| Compound | $IC_{50}$ |
| --- | --- |
| Carnosic acid | 15 μM |
| Nomifensine | 11 nM |

Example 3

Monoamine Oxidase Inhibition by Tricyclic Diterpenes and their Derivatives of the Formula I The organic amines p-tyramine or benzylamine were used as substrates for the Monoamine oxidase A (MAO-A) and B (MAO-B) enzymes respectively. The $H_2O_2$ produced by this reaction was quantified by reaction with vanillic acid, catalysed by horse radish peroxidase (HRP).

The reactions were carried out in polystyrene microtitre plates. The MAO enzymes (final concentration 2 U/ml) were mixed with either p-tyramine (Sigma, final concentration 0.5 mM) or benzylamine (Sigma, final concentration 0.5 mM) as appropriate and the chromogenic solution (containing vanillic acid (Fluka), 4-aminoantipyrine (Fluka) and horse radish peroxidase (Sigma), final concentrations 0.25 mM, 0.125 mM and 1 U/ml respectively) in 0.2 M potassium phosphate buffer, pH 7.6. The reactions were followed in a microtitre plate absorbance reader e.g. Spectramax M5 (Molecular Devices Corporation). Absorbance readings at 495 nm were taken every 15 seconds for 40 minutes and the initial reaction velocities calculated by linear regression using SOFTmaxPro (Molecular Devices Corporation).

The effect of tricyclic diterpenes and their derivatives according to formula I on the monoamine oxidase enzymes was determined by their inclusion in the assay at a range of concentrations between 0.03 and 100 μM for 10 minutes prior to and during the incubation with substrate. To determine the effect of the compounds on the HRP catalyzed portion of the reaction, the MAO enzyme was replaced by $H_2O_2$ (Molecular Probes, final concentration 0.2 mM). The reactions containing MAO-A and MAO-B were both inhibited by tricyclic diterpenes and their derivatives according to formula I in a dose-dependent manner, whilst the control reaction, was unaffected. The measured $IC_{50}$ values for inhibition of monoamine oxidase activity by carnosic acid, carnosic acid-12-methyl ether and 20-deoxo-carnosol are shown in Table 3.

TABLE 3

Inhibition of MAO-A and MAO-B by tricyclic diterpenes and their derivatives of the formula I.

| Substance | $IC_{50}$ [μM] for Inhibition of MAO-A | $IC_{50}$ [μM] for Inhibition of MAO-B |
| --- | --- | --- |
| Carnosic Acid | 4.4 ± 0.3 (n = 3) | 8.6 ± 0.6 (n = 3) |
| 20-Deoxo-carnosol | 4.3 ± 1.1 (n = 2) | 27.0 ± 7.3 (n = 2) |
| Carnosic acid-12-methyl ether | 40.6 ± 0.25 (n = 2) | 83.1 ± 6.8 (n = 2) |

Results are shown as mean ± s.e.m.

Example 4

Porsolt's Swim Test

The Forced Swim Test (FST) was first reported in 1977 for screening of antidepressant-like compounds in rats (Porsolt et al 1977 *Nature* 266:730-732) and, later, modified for testing mice (Porsolt et al, *Arch. Int Pharmacodynamie*, 229:327-336.). "Behavioural despair" was demonstrated whereby, when forced to swim in a cylinder of water from which there is no escape, rats or mice will initially exhibit vigorous, escape-oriented, activity but eventually only make those minimal movements necessary to keep their heads above water. The test was shown to be sensitive to a range of drugs with known therapeutic activity against depression, some of which had not previously shown efficacy in the existing behavioural models Carnosic Acid Mice were individually placed in cylinders (24.5 cm height, 19.5 cm internal diameter) containing 13.5 cm depth of water (22±0.5° C.) for a period of 6 minutes, behavioural parameters of interest being analysed during the final 4 minutes of the test, since the first 2 minutes include vigorous activity. Six cylinders were placed in a Perspex box, thus enabling six mice to be tested simultaneously.

Automatic monitoring of swim tests was enabled through the use of VideoMot2 software (TSE Technical and Scientific Equipment GmbH, Bad Homburg, Germany). All experiments were observed via a black and white CCD camera. The rest:locomotion and stop:start thresholds, as determined by setting parameters in the software programme, determine the number of pixels which must change for a movement to be registered, enabling the software to determine whether a mouse is swimming or resting. The parameters which are automatically recorded include: rest time and locomotion time (ms), % rest and % locomotion, distance traveled (cm), speed of travel (cm/s) and number of stops.

Carnosic acid was evaluated at 10, 20 and 30 mg/kg (i.p., 30 min prior to the test) and at 200 mg/kg (p.o., 24, 5 and 1 h prior to the test) and was compared with a vehicle control group and two reference compounds: the selective serotonin reuptake inhibitor (SSRI), fluoxetine (10 mg/kg), and the tricyclic antidepressant, imipramine (32 mg/kg). Data were analysed by comparing treated groups with the untreated control group using Fisher's PLSD (StatView, SAS Institute Inc., Cary, N.C., USA)

Results

TABLE 4

Effects of carnosic acid, fluoxetine and imipramine in the FST in the mouse, following either i.p. (−30 min) or p.o. (−24, −5, −1 h) administration.

| Treatment | | | Duration of immobility (% change from control) |
| --- | --- | --- | --- |
| carnosic acid | 10 mg/kg | i.p., −30 min | −29% * |
| carnosic acid | 20 mg/kg | i.p., −30 min | −30% * |
| carnosic acid | 30 mg/kg | i.p., −30 min | −29% * |
| fluoxetine | 10 mg/kg | i.p., −30 min | −41% ** |
| imipramine | 32 mg/kg | i.p., −30 min | −61% *** |
| carnosic acid | 200 mg/kg | p.o., −24, −5, −1 h | −38% ** |
| imipramine | 32 mg/kg | p.o., −24, −5, −1 h | −56% *** |

Duration of immobility is shown as % change from control, where
* $p < 0.05$,
** $p < 0.01$,
*** $p < 0.001$ (Fisher's PLSD).

Thus, all doses of carnosic acid tested in the FST, following both i.p. and p.o. administration, significantly reduced immobility behaviour to a comparable extent as both of the reference compounds, thus indicating antidepressant-like activity.

Example 5

Marble Burying Test

"Defensive burying" behaviour was demonstrated by rats burying noxious objects, such as drinking spouts filled with an unpleasant-tasting liquid (Wilkie et al 1979 *J Exp Anal Behav,* 31:299-306.) or shock prods (Pinel et al 1978. *J. Comp Phys Physchol* 92: 708-712.). The marble burying test was devised as a modification of such a test. Poling et al. 1981 *J Exp Anal of Behav* 35:31-44, exposed rats to individual cages each containing 25 marbles, daily for 10 or 21 consecutive days. The number of marbles buried, on each day of the 10 day (d) period, or 24 hours (h) after the 21 d exposure, were counted. The authors reported that the burying of marbles was not determined by novelty, or due to any noxious stimuli.

Marble burying behaviour by mice is reported to be sensitive to a range of minor (e.g. diazepam) and major (e.g. haloperidol) tranquilisers (Broekkamp et al 1986 *Eur J Pharma,* 126:223-229.), in addition to SSRIs (e.g. fluvoxamine, fluoxetine, citalopram), tricyclic antidepressants (e.g. imipramine, desipramine) and selective noradrenaline uptake inhibitors (e.g. reboxetine), at doses which do not induce sedation. The model may reflect either anxiety-like- or obsessive-compulsive-behaviour (see DE BOER et al 2003 *Eur J Pharmacol* 463:145-161.).

The method applied here follows that described by Broekkamp et al., supra. Mice (n=15 per treatment group) were individually placed in transparent plastic cages (33×21× 18 cm) with 5 cm of sawdust on the floor and 25 marbles (diameter 1 cm) grouped in the centre of the cage. A second, up-turned, cage served as a lid. The number of marbles covered by sawdust (by at least two-thirds) was counted at the end of the 30-minute test period. Tests were performed by investigators blind to the drug treatment protocol. Prior to testing, all test cages and marbles were "impregnated" by leaving 10 naive mice in each cage for 15 minutes.

Carnosic acid (3, 10 and 30 mg/kg) and 20-deoxy-carnosol (30, 100 and 200 mg/kg) were administered intraperitoneally (i.p.) 30 minutes before the test, and compared with a vehicle control group. Fluoxetine (32 mg/kg) and venlafaxine (16 mg/kg; selective serotonin/noradrenaline reuptake inhibitor), administered under the same experimental conditions, were used as reference substances.

Data were analysed by comparing treated groups with vehicle control using unpaired Student's t-tests.

Results

TABLE 5

Effects of carnosic acid and fluoxetine in the marble burying test in the mouse, following acute, i.p., administration.

| Carnosic acid | NUMBER OF MARBLES COVERED BY SAWDUST | | |
| --- | --- | --- | --- |
| (mg/kg) i.p. −30 min | mean ± s.e.m. | p value | % change from control |
| Vehicle | 23.7 ± 0.5 | — | — |
| 3 | 21.9 ± 1.3 (NS) | 0.2071 | −8% |
| 10 | 22.7 ± 0.5 (NS) | 0.1413 | −4% |
| 30 | 8.7 ± 2.9 (***) | <0.0001 | −63% |
| FLUOXETINE | | | |
| 32 mg/kg i.p. −30 min | 0.0 ± 0.0 (***) | <0.0001 | −100% |

The number of marbles buried is shown as % change from control, where (NS) = non-significant, TABLE 5-continued Effects of carnosic acid and fluoxetine in the marble burying test in the mouse, following acute, i.p., administration.

| Carnosic acid | NUMBER OF MARBLES COVERED BY SAWDUST | | |
| --- | --- | --- | --- |
| (mg/kg) i.p. −30 min | mean ± s.e.m. | p value | % change from control |

(***) $p < 0.001$ (Student's t-test).

The highest dose of carnosic acid tested (30 mg/kg) clearly and significantly reduced marble burying behaviour, in a similar manner to the SSRI fluoxetine, thus indicating anxiolytic-like activity.

TABLE 6

Effects of 20-deoxy-carnosol and fluoxetine in the marble burying test in the mouse, following acute, i.p., administration.

| 20-Deoxy-carnosol | NUMBER OF MARBLES COVERED BY SAWDUST | | |
| --- | --- | --- | --- |
| (mg/kg) i.p. −30 min | mean ± s.e.m. | p value | % change from control |
| Vehicle | 21.9 ± 0.8 | — | — |
| 30 | 16.7 ± 2.2 * | 0.0329 | −24% |
| 100 | 9.7 ± 2.3 *** | <0.0001 | −56% |
| 200 | 8.8 ± 2.4 *** | <0.0001 | −60% |
| FLUOXETINE | | | |
| 32 mg/kg i.p. −30 min | 0.0 *** | <0.0001 | −100% |
| VENLAFAXINE | | | |
| 16 mg/kg i.p. −30 min | 8.7 ± 2.2 *** | <0.0001 | −60% |

The number of marbles buried is shown as % change from control, where
* $p < 0.05$,
*** $p < 0.001$ (Student's t-test).

20-deoxy-carnosol dose-dependently and significantly reduced marble burying behaviour in a similar manner to the SSRI fluoxetine and to the same extent as the selective serotonin/noradrenaline-reuptake inhibitor venlafaxine, thus indicating anxiolytic-like activity.

Example 6

Effect of Carnosic Acid in the Light Dark Box Test in the Mouse after Subchronic, Oral Gavage The method, which detects anxiolytic activity, follows that described by Crawley, 1981 *Pharmacol. Biochem. Behav.,* 15:695-699. Anxiolytics increase the time spent in the light compartment.

Animals were placed into the light compartment of a 2-compartment box with one half light and open (25×27×27 cm) and the other half dark and closed (20×27×27 cm). The time spent in each compartment as well as the number of times the animal crosses from one side to the other is scored during a 3-minute test. 15 mice were studied per group. The test was performed blind.

Carnosic acid was evaluated at 3 doses (100, 200, 400 mg/kg BW), administered by oral gavage (p.o.) 24, 5 and 1 hour before the test, and compared with a vehicle control group (corn oil). Carnosic acid was dissolved in corn oil ("vehicle"). Clobazam (32 mg/kg p.o.), administered 1 hour before the test, was used as reference substance. Mice in this group received additional administrations of vehicle at 24 and 5 hours before the test in order to maintain experimental blinding.

TABLE 7

Effects of carnosic acid and clobazam on behaviour in the light-dark box test in the mouse, following subchronic, p.o., administration.

| TREATMENT (mg/kg) p.o. −24, −5, −1 h | TIME SPENT IN THE LIGHT COMPARTMENT % change from control | | NUMBER OF CROSSINGS % change from control | |
|---|---|---|---|---|
| Carnosic acid (100) | +19% | NS | +17% | NS |
| Carnosic acid (200) | +10% | NS | −21% | NS |
| Carnosic acid (400) | +38% | * | +23% | NS |
| Clobazam (32; −1 h) | +43% | ** | +56% | * |

Time spent in the light compartment and number of crossings are shown as % change from control, where NS = non-significant,
* $p < 0.05$,
** $p < 0.01$ (Student's t-test).

Carnosic acid (100, 200 and 400 mg/kg) globally increased the time spent in the light compartment, as compared with vehicle control (+19%, +10% and +38%, respectively), significantly so at 400 mg/kg ($p<0.05$). It did not affect the number of crossings.

Example 7

Preparation of a Soft Gelatine Capsule

A soft gelatine capsule (500 mg) is prepared comprising the following ingredients:

| Ingredient | Amount per Capsule |
|---|---|
| Carnosic acid | 200 mg |
| Lecithin | 50 mg |
| Soy bean oil | 250 mg |

Two capsules per day for 3 months may be administered to a human adult for the treatment of mild chronic dysthymia.

Example 8

Preparation of a Soft Gelatine Capsule

A soft gelatine capsule (600 mg) is prepared comprising the following ingredients:

| Ingredient | Amount per Capsule |
|---|---|
| Carnosic acid | 200 mg |
| Evening prim rose oil | 300 mg |
| Vitamin $B_6$ | 100 mg |

One capsule per day preferably at the second half of the menstrual cycle should be taken for 14 days for the treatment of premenstrual syndrome and premenstrual dysphoric disorder.

Example 9

Preparation of a Tablet

A 400 mg-tablet is prepared comprising the following ingredients:

| Ingredient | Amount per tablet |
|---|---|
| Carnosic acid | 100 mg |
| Passion flower standardized extract | 150 mg |
| Green Tea Extract, e.g. TEAVIGO ® from DSM Nutritional Products, Kaiseraugst, Switzerland | 150 mg |

For general well being, energizing and stress alleviation, one tablet is taken twice daily for 3 months.

Example 10

Preparation of an Instant Flavoured Soft Drink

| Ingredient | Amount [g] |
|---|---|
| Carnosic acid | 0.9 |
| Sucrose, fine powder | 922.7 |
| Ascorbic acid, fine powder | 2.0 |
| Citric acid anhydrous powder | 55.0 |
| Lemon flavour | 8.0 |
| Trisodium citrate anhydrous powder | 6.0 |
| Tricalciumphosphate | 5.0 |
| β-Carotene 1% CWS from DNP AG, Kaiseraugst, Switzerland | 0.4 |
| Total amount | 1000 |

All ingredients are blended and sieved through a 500 μm sieve. The resulting powder is put in an appropriate container and mixed on a tubular blender for at least 20 minutes. For preparing the drink, 125 g of the obtained mixed powder are taken and filled up with water to one litre of beverage.

The ready-to-drink soft drink contains ca. 30 mg carnosic acid per serving (250 ml).

As a strengthener and for general well being 2 servings per day (240 ml) should be drunk.

Example 11

Preparation of a Fortified Non Baked Cereal Bar

| Ingredient | Amount [g] |
|---|---|
| Carnosic acid | 0.95 |
| Sugar | 114.55 |
| Water | 54.0 |
| Salt | 1.5 |
| Glucose syrup | 130.0 |
| Invert sugar syrup | 95.0 |
| Sorbitol Syrup | 35.0 |
| Palmkernel fat | 60.0 |
| Baking fat | 40.0 |
| Lecithin | 1.5 |
| Hardened palm-oil | 2.5 |
| Dried and cut apple | 63.0 |
| Cornflakes | 100.0 |
| Rice crispies | 120.0 |
| Wheat crispies | 90.0 |
| Roasted hazelnut | 40.0 |
| Skim milk powder | 45.0 |
| Apple flavour 74863-33 | 2.0 |
| Citric acid | 5.0 |
| Total amount | 1000 |

Carnosic acid is premixed with skim milk powder and placed in a planetary bowl mixer. Cornflakes and rice crispies are added and the total is mixed gently. Then the dried and cut apples are added. In a first cooking pot sugar, water and salt are mixed in the amounts given above (solution 1). In a second cooking pot glucose, invert and sorbitol syrup are mixed in the amounts given above (solution 2). A mixture of baking fat, palmkernel fat, lecithin and emulsifier is the fat phase. Solution 1 is heated to 110° C. Solution 2 is heated to 113° C. and then cooled in a cold water bath. Afterwards solution 1 and 2 are combined. The fat phase is melted at 75° C. in a water bath. The fat phase is added to the combined mixture of solution 1 and 2. Apple flavour and citric acid are added to the liquid sugar-fat mix. The liquid mass is added to the dry ingredients and mixed well in the planetary bowl mixer. The mass is put on a marble plate and rolled to the desired thickness. The mass is cooled down to room temperature and cut into pieces. The non baked cereal bar contains ca. 25 mg carnosic acid per serving (30 g). For general wellbeing and energizing 1-2 cereal bars should be eaten per day.

What is claimed is:

1. A method of enhancing neurotransmission wherein the neurotransmission effect is selected from the group consisting of: an antidepressant, mood/vitality improver, stress reliever, condition improver, reducer of anxiety, reducer of obsessive-compulsive behaviour, relaxant, sleep improver and/or insomnia alleviator comprising:
   administering a dietary or pharmaceutical composition containing
   0.001 mg per kg body weight to about 20 mg per kg body weight per day of a compound selected from the group consisting of: carnosic acid 12-methyl ether, 7-oxocallitrisic acid, totarol, 16-hydroxytotarol, totarol-19-carboxylic acid methyl ester, 20-deoxo-carnosol, 7-methyfrosmanol, sageone, 8,11,13-abietatriene-11,12,20-triol, royleanonic acid and ferruginol to a healthy person in need thereof; or
   0.001 mg per kg bodyweight to 1000 mg per kg bodyweight per day to an animal excluding humans in in need thereof
   and observing an enhanced neurotransmission effect.

2. A method according to claim 1 wherein the composition is in the form of a food, a fortified food, a dietary supplement, a non-alcoholic drink, a sport drinks, a fruit juice, a lemonades, a near-water drink, a tea a milk based drinks, a liquid food or a dairy product.

3. A method according to claim 1 wherein 0.01 to 10 mg per kg body weight is administered to the person.

4. A method according to claim 1 wherein 0.05 to 5.0 mg per kg body weight is administered to the person.

5. A method according to claim 1 wherein 0.1 mg to 500 mg per kg body weight is administered to the animal.

6. A method according to claim 1 wherein 1 mg to 100 mg per kg body weight is administered to the animal.

7. A method of enhancing neurotransmission wherein the neurotransmission effect is selected from the group consisting of: an antidepressant, mood/vitality improver, stress reliever, condition improver, reducer of anxiety, reducer of obsessive-compulsive behaviour, relaxant, sleep improver and/or insomnia alleviator
   comprising:
   administering a dietary or pharmaceutical composition containing
   0.1 mg to 1000 mg of a compound selected from the group consisting of: carnosic acid 12-methyl ether, 7-oxocallitrisic acid, totarol, 16-hydroxytotarol, totarol-19-carboxylic acid methyl ester, 20-deoxo-carnosol, 7-methylrosmanol, sageone, 8,11,13-abietatriene-11,12,20-triol, royleanonic acid and ferruginol to a healthy person in need thereof;
   and observing an enhanced neurotransmission effect.

8. A method according to claim 7 wherein 1 mg to 500 mg of the compound is administered.

9. A method of enhancing neurotransmission wherein the neurotransmission effect is selected from the group consisting of: an antidepressant, mood/vitality improver, stress reliever, condition improver, reducer of anxiety, reducer of obsessive-compulsive behaviour, relaxant, sleep improver and/or insomnia alleviator comprising:
   administering a food or beverage comprising 0.0001 (1 mg/kg) to 5 weight % (50g/kg) of a compound, based on the total weight of the food or beverage, wherein the compound is selected from the group consisting of
   carnosic acid 12-methyl ether, 7-oxocallitrisic acid, totarol, 16-hydroxytotarol, totarol-19-carboxylic acid methyl ester, 20-deoxo-carnosol, 7-methylrosmanol, sageone, 8,11,13-abietatriene-11,12,20-triol, royleanonic acid and ferruginol to a healthy person in need thereof.

10. A method according to claim 9 wherein the food or beverage comprises 0.01% (10 mg/kg) to 1 weight-% (10 g/kg) compound.

11. A method according to claim 9 wherein the food or beverage comprises 0.01 (100 mg/kg) to about 0.5weight-% (5g/kg) compound.

12. A method according to claim 9 wherein the amount of the compound is 10 to 30 mg per serving.

* * * * *